(12) United States Patent
Hogendoorn et al.

(10) Patent No.: US 10,393,559 B2
(45) Date of Patent: Aug. 27, 2019

(54) METHOD FOR OPERATING A NUCLEAR MAGNETIC FLOWMETER AND NUCLEAR MAGNETIC FLOWMETER

(71) Applicant: Krohne AG, Basel (CH)

(72) Inventors: Cornelis Johannes Hogendoorn, Spijk (NL); Lucas Matias Ceferino Cerioni, Dordrecht (NL); Rutger Reinout Tromp, Dordrecht (NL); Marco Leendert Zoeteweij, Heindrik-Ido-Ambach (NL); Olaf Jean Paul Bousché, Dordrecht (NL)

(73) Assignee: KROHNE AG, Basel (CH)

( * ) Notice: Subject to any disclaimer, the term of this patent is extended or adjusted under 35 U.S.C. 154(b) by 54 days.

(21) Appl. No.: 15/507,423

(22) PCT Filed: Jul. 2, 2015

(86) PCT No.: PCT/EP2015/065138
§ 371 (c)(1),
(2) Date: Feb. 28, 2017

(87) PCT Pub. No.: WO2016/030059
PCT Pub. Date: Mar. 3, 2016

(65) Prior Publication Data
US 2017/0284847 A1    Oct. 5, 2017

(30) Foreign Application Priority Data

Aug. 29, 2014  (DE) .......................... 10 2014 012 574
Feb. 2, 2015   (DE) .......................... 10 2015 001 161

(51) Int. Cl.
*G01V 3/00*    (2006.01)
*G01F 1/716*   (2006.01)
(Continued)

(52) U.S. Cl.
CPC ............... *G01F 1/716* (2013.01); *G01F 1/74* (2013.01); *G01F 25/0007* (2013.01);
(Continued)

(58) Field of Classification Search
CPC .. G01R 33/383; G01R 33/445; G01R 33/448; G01R 33/50; G01R 33/5617;
(Continued)

(56) References Cited

U.S. PATENT DOCUMENTS 4,769,602 A     9/1988  Vinegar et al.
6,255,818 B1 *  7/2001  Heaton ................ G01R 33/563
                                                          324/303

(Continued)

FOREIGN PATENT DOCUMENTS

DE    41 19 711 A1    12/1992
GB    2 342 170 A     4/2000
(Continued)

OTHER PUBLICATIONS

T. Dyakowski; Process Tomography Applied to Multi-Phase Flow Measurement; Measurement Science and Technology, IOP, Bristol, GB, vol. 7, No. 3, Mar. 1, 1996, pp. 343-353.
(Continued)

*Primary Examiner* — Rodney E Fuller
(74) *Attorney, Agent, or Firm* — David S. Safran; Roberts Mlotkowski Safran Cole & Calderon, P.C.

(57) ABSTRACT

A method for measuring the flow rate of a multi-phase medium flowing through a measuring tube using a nuclear magnetic resonance flow meter can be used to measure the flow rate of a multi-phase medium in a simplified manner. For this purpose, a measuring device is used which implements, at the end of each pre-magnetization path, 2D tomography in the measurement tube cross-sectional plane with stratification in the z direction; the measurement tube cross-
(Continued)

sectional plane is subdivided into layers that are thin compared to the measurement tube diameter; nuclear magnetic resonance measurements are carried out in every layer to determine measurement signals, using pre-magnetization paths of different lengths; the flow rates are measured in every layer based on the measurement signals; and the time is determined from the signal ratios of the amplitudes of the measurement signals in every layer.

17 Claims, 2 Drawing Sheets

(51) Int. Cl.
G01N 24/08 (2006.01)
G01F 1/74 (2006.01)
G01R 33/50 (2006.01)
G01R 33/563 (2006.01)
G01F 25/00 (2006.01)
G01R 33/30 (2006.01)
G01F 1/56 (2006.01)
G01R 33/44 (2006.01)

(52) U.S. Cl.
CPC ........... G01N 24/08 (2013.01); G01R 33/307 (2013.01); G01R 33/50 (2013.01); G01R 33/56308 (2013.01); G01F 1/56 (2013.01); G01R 33/44 (2013.01)

(58) Field of Classification Search
CPC ........... G01R 33/563; G01R 33/56308; G01R 33/56341; E21B 49/08; G01F 1/716; G01F 1/74; G01N 24/081; G01N 24/08; G01N 24/082; G01N 24/085; G01V 3/32
USPC .......................................................... 324/309
See application file for complete search history.

(56) References Cited

U.S. PATENT DOCUMENTS

| 7,872,474 | B2 | 1/2011 | Pusiol et al. |
| 8,633,689 | B2 | 1/2014 | Li et al. |
| 2005/0216196 | A1* | 9/2005 | Akkurt .................... E21B 49/08 702/6 |
| 2008/0174309 | A1* | 7/2008 | Pusiol ...................... G01F 1/56 324/306 |
| 2010/0088033 | A1* | 4/2010 | Chen .................... G01N 24/081 702/8 |
| 2012/0092007 | A1* | 4/2012 | Li ........................... G01F 1/716 324/306 |
| 2013/0113480 | A1* | 5/2013 | Kadayam Viswanathan ............... G01V 3/32 324/303 |
| 2015/0219782 | A1* | 8/2015 | Kadayam Viswanathan ............... G01V 3/32 324/309 |
| 2015/0234026 | A1* | 8/2015 | Hogendoorn ........ G01R 33/563 324/306 |
| 2016/0011032 | A1* | 1/2016 | Hogendoorn ............. G01F 1/74 324/306 |

FOREIGN PATENT DOCUMENTS

| GB | 2 432 003 A | 5/2007 |
| WO | 91/18280 A1 | 11/1991 |

OTHER PUBLICATIONS

N. Reinecke, G. Petritsch, M. Boddem and D. Mewes; Tomographic Imaging of the Phase Distribution in Two-Phase Slug Flow; International Journal of Multiphase Flow, Dec. 31, 1996, vol. 24, No. 4, pp. 617-634.

\* cited by examiner

METHOD FOR OPERATING A NUCLEAR MAGNETIC FLOWMETER AND NUCLEAR MAGNETIC FLOWMETER

BACKGROUND OF THE INVENTION

Field of the Invention

The invention initially relates to a method for determining the flow of a multi-phase medium flowing through a measuring tube with a nuclear magnetic flowmeter having a pre-magnetization device and a measuring device, wherein the pre-magnetization device implements at least two pre-magnetization sections of differing lengths with the lengths $L_1, L_2, \ldots$. Furthermore, the invention relates to a nuclear magnetic flowmeter, in particular for use in conjunction with the method according to the invention.

Description of Related Art

Nuclear magnetic flowmeters, which are designed for determining the flow of a medium flowing through a measuring tube, are used, in particular, when the medium contains several phases. Determining the flow of a multi-phase medium also includes, in addition to determining flow velocity and flow rate, determining the portions of the individual phases of the medium. However, determining the flow of a single-phase medium is also possible using a nuclear magnetic flowmeter.

The prerequisite for applicability of nuclear magnetic measuring methods is that the medium or each phase of the medium has atomic nuclei with magnetic moments.

In order to differentiate between individual phases, it is additionally necessary that the individual phases have differentiable relaxation times. Presently, the so-called spin-lattice relaxation time $T_1$, also called $T_1$ time, is of particular importance.

If a system containing an atomic nucleus bearing a magnetic moment is located in an external magnetic field exhibiting a specific direction, then the magnetic moments of the atomic nuclei are aligned in the external magnetic field. The magnetic moments take up a state that is parallel or anti-parallel to the external magnetic field, wherein there is a higher probability that the state parallel to the external magnetic field is filled, so that a "net magnetization" parallel to the external field is formed in the system. This "net magnetization" is also called equilibrium magnetization. The magnetization can be deflected out of its equilibrium position by an external interference. However, as soon as the interference is gone, the magnetization strives to return to its equilibrium position, to relax again in its equilibrium position. The time that is necessary for this to take place is the spin-lattice relaxation time $T_1$.

The spin-lattice relaxation time $T_1$ has a different value for each phase in a multi-phase medium, as already described above. Accordingly, the $T_1$ time is an important distinguishing and characterizing parameter of each phase. In particular, the knowledge of the $T_1$ time is a good basis for making complete characterization of the medium possible. Determining the $T_1$ time is often relatively complicated and, above all, very time-consuming.

It is to be pointed out here that multi-phase mediums extracted from oil sources consist essentially of the two liquid phases crude oil and saltwater, and of the gaseous phase natural gas, wherein all three phases contain hydrogen nuclei that bear a magnetic moment.

Nuclear magnetic flowmeters known from the prior art, which are used for determining the flow of a multi-phase medium flowing through a measuring tube, can be designed so that they include a pre-magnetization device and a measuring device, wherein the pre-magnetization device implements at least two pre-magnetization sections with different lengths $L_1, L_2, \ldots$.

SUMMARY OF THE INVENTION

The object of the present invention is to provide a method for operating a nuclear magnetic flowmeter, with which the flow of a multi-phase medium can be determined in a manner that is simplified compared to the prior art.

A first method according to the invention is characterized in that one measuring device is used that implements 2D tomography at the end of each pre-magnetization section in a measuring plane perpendicular to the longitudinal axis of the measuring tube, that the measuring planes are identically divided into voxels, that the dimensions of the voxels are chosen such that only one phase of the medium flows in each voxel, that nuclear magnetic measurement is carried out for determining measuring signals, that the flow velocity of the medium is determined in each voxel in each measuring plane, that the average flow velocity of the medium for each voxel over all measuring planes is determined from the determined values of the flow velocity of each corresponding voxel of the individual measuring planes, that the signal ratio of the measuring signals of each corresponding voxel of the different measuring planes to one another is determined and that, with the known values for the lengths $L_1, L_2, \ldots$ of the pre-magnetization section, the $T_1$ times in each voxel are determined using the signal ratios.

A preferred implementation of the method according to the invention is characterized in that, in a further—in particular subsequent—step, the respective hydrogen index in each voxel is determined with the respective $T_1$ times and that using the $T_1$ times and the hydrogen index HI, the different phases of the medium and the sections of the different phases are determined.

A further preferred implementation of the method according to the invention is characterized in that the flow rates are determined by integration over the different sections of the medium and multiplication with the respective flow velocities. This implementation has the great advantage that the flow rates of the individual phases of the medium can be determined using only the knowledge of the "expansion of the sections of the individual phases" and the respective flow velocities.

A particular preferred implementation of the method according to the invention is characterized in that the nuclear magnetic measurement is implemented with a CPMG sequence. However, it should be noted that any pulse sequence suitable for nuclear magnetic measurement can be used.

The velocity of the medium in each voxel can be determined, in one implementation of the method according to the invention, using the "convective decay" method. The medium is excited in the measuring section in the measuring device in this method and the measuring signals transmitted by the excited medium are repeatedly consecutively measured. Since the excited section flows out of the measuring section bit by bit into the measuring device, i.e., the amount of excited nuclear spin located in the measuring section sinks, the measuring signal becomes weaker with each measurement occurrence. The flow velocity can be determined using the decrease of the signal strength.

A further, preferred implementation of the method according to the invention is characterized in that the amplitudes of the measuring signals at time t=0 are used for determining the signal ratios. Hereby, the time t=0 is defined as the beginning of a measurement.

A particular implementation of the method according to the invention is characterized in that the temporal course of the measuring signals is used for determining the signal ratio. This is possible since, on the one hand, the medium is in a single-phase state in each voxel, i.e., only one single phase of the medium appears in one voxel, because the spin-spin relaxation time $T_2$, which depends on the phase of the medium, is identical in each corresponding voxel of the different measuring planes; on the other hand, the velocity of the medium in the respective corresponding voxels of the different measuring planes can be assumed to be identical.

In turn, a particular implementation of the method according to the invention is characterized in that the at least two pre-magnetization sections are implemented by variable RF coils and that the measuring planes at the end of each pre-magnetization section are realized by different planes. In particular, thus, the at least two pre-magnetization sections can have the same starting point—preferably, the starting point of a pre-magnetization section is the point at which the pre-magnetization device sets in. The measuring planes located in the measuring device are, thus, implemented as two different measuring planes and are located in the area of the respective RF coil.

Another preferred implementation of the method according to the invention is characterized in that the at least two pre-magnetization sections are implemented by rotating magnetic arrangements and that the measuring planes at the end of each pre-magnetization section are realized in one single spatial plane. Thus, the at least two measuring planes at the end of the respective pre-magnetization section coincide spatially. A simple construction of the measuring device can be implemented using this design according to the invention.

In a further implementation, it is provided that the at least two pre-magnetization sections are implemented by RF coils transmitting spoil pulses and that the measuring planes at the end of each pre-magnetization section are realized in one single spatial plane. A spoil pulse, here, is a pulse or pulse sequence that destroys the magnetization of the medium in the z direction. The RF coils transmitting the spoil pulses are arranged in the area of the pre-magnetization device. Each of the RF coils defines the beginning of a pre-magnetization section, since magnetization is reconstructed after spoiling, such as though the medium was flowing into the pre-magnetization device. This implementation also has the advantage that the at least two measuring planes at the end of each pre-magnetization section coincide spatially.

The object described above is further achieved in that a method is applied for determining the flow of a multi-phase medium flowing through a measuring tube with a nuclear magnetic flowmeter having a pre-magnetization device and a measuring device, wherein the pre-magnetization device implements at least two pre-magnetization sections with different lengths with the lengths $L_1$, $L_2$, . . . that is characterized in that that a measuring device is used that implements 2D tomography at the end of each pre-magnetization section in the measuring tube cross sectional plane with slicing in the z direction, that the measuring tube cross sectional plane is divided into thin layers in relation to the measuring tube diameter, that nuclear magnetic measurements are carried out in every layer for determining measuring signals with at least two pre-magnetization sections of different lengths, that the flow velocity in each individual layer is determined using the measuring signals and that the $T_1$ time is determined using the signal ratios of the amplitudes of the measuring signals in each layer.

A particular implementation of the last-described method according to the invention is characterized in that the portions of the individual phases in the medium are determined using the absolute amplitudes of the measuring signals.

The last-described method according to the invention is suitable, in particular, for flow measurement of multi-phase media, in which the individual phases of the medium have different flow velocities. In such a case, it is possible that a faster-flowing phase passes a slower-flowing phase, this is a so-called "phase slip". Disregarding different phase velocities, i.e., the assumption that there is only one phase velocity in the medium, results in inaccuracies and measuring error. Since the layers, in which the measurements are carried out, are chosen to be thin in relation to the measuring tube cross section, the assumption is justified that each layer contains only one single phase, i.e., a phase slip does not occur within one layer.

A further problem in flow measurement of multi-phase media is based on the difficulty of measuring the gas portion, since gas has a very small measuring signal. Thus, a further preferred implementation of the method according to the invention, which has been seen to be advantageous for such media having slug flow or a stratified flow profile, is characterized in that the water to liquid ratio for the lower layers in the measuring tubes are determined layer for layer from bottom to top in the measuring tube, that a water to liquid curve depending on the position of the layer in the measuring tube is generated using the determined values, that the curve is extrapolated based on the last determined value over the entire measuring tube cross section, that the expected measuring signal amplitudes for the upper layers in the measuring tube are calculated from the extrapolated curve and that the gas volume portion in the upper layers is determined using the difference between the expected measuring signal amplitude and the actual measuring signal amplitude.

In the layers in the lower area of the measuring tube, there is no gas in the case of slug flow or in stratified flow. Accordingly, the signal is determined solely using the liquid portion of the medium, $\alpha_O + \alpha_W = 1$. Hence, it is possible to use the absolute amplitudes for determining the portions of the phases in the medium and, in particular, to determine the water to liquid ratio. Hereby, the signal for oil is stronger than the signal for water. A greater water to liquid ratio, thus, corresponds to a weaker measuring signal (provided that $\alpha_O + \alpha_W = 1$). In all probability, however, gas is likely to be found in the upper layers of the measuring tube. Since gas has a very weak signal, the overall signal in gaseous layers will also be weak compared to gas-free layers. A weak measuring signal corresponds to a small measuring signal amplitude, while a strong measuring signal corresponds to a large measuring signal amplitude. The gas portion of the medium can be calculated using the theoretically calculated measuring signal amplitudes under the assumption that there is no gas in the upper layers and the measured measuring signal amplitudes with the 1-α method, in which the measured measuring signal amplitudes are subtracted from the theoretically calculated measuring signal amplitudes.

Additionally, it is the object of the invention to provide a nuclear magnetic flowmeter, with which the flow of a multi-phase medium can be determined in a simplified manner.

The above object is initially and essentially achieved in that the measuring device implements 2D tomography at the end of each pre-magnetization section either in one measuring plane perpendicular to the longitudinal axis of the measuring tube or in the measuring tube cross sectional plane with slicing in the z-direction.

Thus, at least two pre-magnetization sections having different lengths are provided in the nuclear magnetic flowmeter according to the invention, accordingly at least two measuring planes are provided according to the invention. In particular, it is possible to provide more than two pre-magnetization sections and measuring planes.

A particular design of the flowmeter according to the invention is characterized in that the different lengths $L_1$, $L_2$, ... of the pre-magnetization section are implemented by variable RF coils and that the measuring planes at the end of every pre-magnetization section fall in the area of the respective RF coil.

A further design of the flowmeter according to the invention is characterized in that the different lengths $L_1$, $L_2$, ... of the pre-magnetization section are implemented by rotating magnetic arrangements and that the measuring planes at the end of each pre-magnetization section are realized in one single spatial plane.

A preferred design of the flowmeter according to the invention is characterized in that the different lengths $L_1$, $L_2$, ... of the pre-magnetization section are implemented by RF coils transmitting spoil pulses and that the measuring planes at the end of each pre-magnetization section are realized in one single spatial plane.

In detail, there are various possibilities for designing and further developing the nuclear magnetic flowmeter according to the invention. Reference is made to the patent claims subordinate to patent claim 14 as well as to the description in conjunction with the drawing. The drawing shows

DETAILED DESCRIPTION OF THE INVENTION

Figure 1:
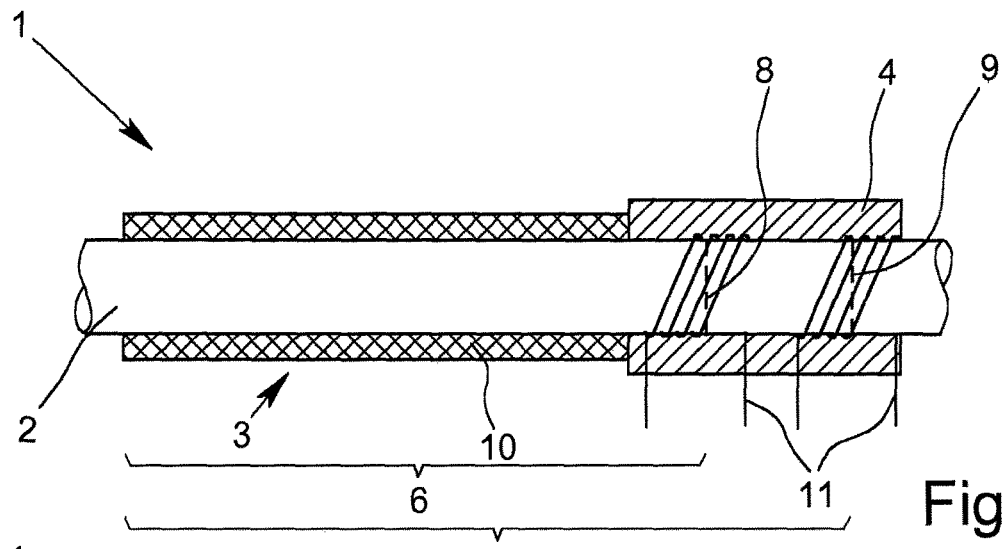
FIG. 1 is a schematic illustration of a first preferred embodiment of the nuclear magnetic flowmeter according to the invention.

A first embodiment of the nuclear magnetic flowmeter 1 according to the invention is illustrated in FIG. 1. The medium, of which the flow is to be measured, flows through the measuring tube 2. The flowmeter 1 includes a pre-magnetization device 3, wherein the pre-magnetization device 3 includes one or more permanent magnets 10 for generation of a magnetic field interfusing the measuring tube 2, as well as a measuring device 4. Two variable RF coils 11 are arranged in the area of the measuring device 4. The variable RF coils 11 are used for exciting the medium with excitation signals and for receiving measuring signals transmitted from the medium due to excitation signals. A first measuring plane 8, perpendicular to the longitudinal axis of the measuring tube, is located in the first variable RF coil 11. The first pre-magnetization section 6 is thus defined as the section from the beginning of the pre-magnetization device 3 to the first measuring plane 8. A second measuring plane 9, which is also perpendicular to the longitudinal axis of the measuring tube, is located in the second variable RF coil 11. Hence, the second pre-magnetization section 7 is defined as the section from the beginning of the pre-magnetization device 3 to the second measuring plane 9. Since the first measuring plane 8 and the second measuring plane 9 do not spatially coincide with one another, the lengths of the first pre-magnetization section 6 and the second pre-magnetization section 7 are different. 2D tomography is implemented in the measuring planes 8 and 9. It is also possible to implement tomography with slicing in the z direction.

Figure 2:
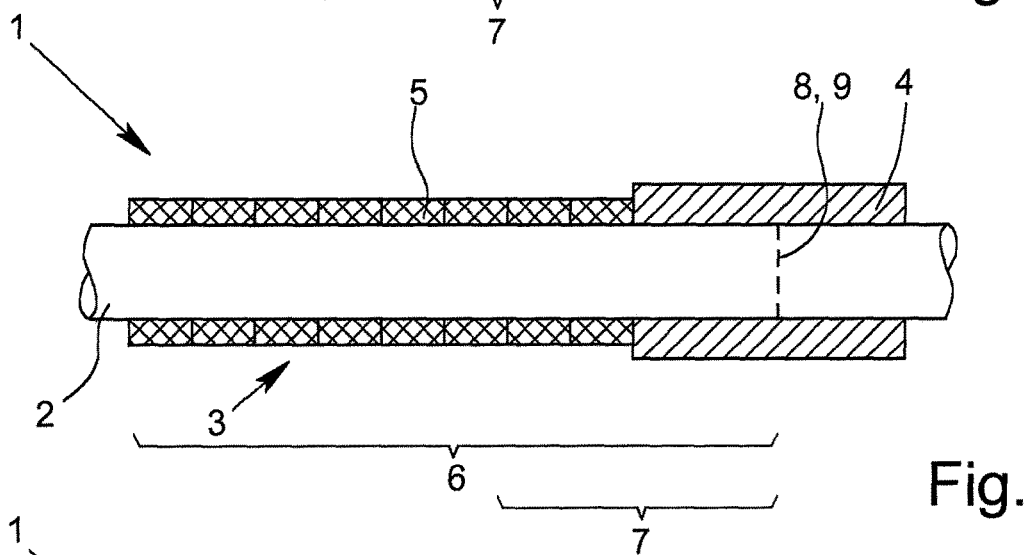
FIG. 2 is a schematic illustration of a second preferred embodiment of the nuclear magnetic flowmeter according to the invention.

A second embodiment of the nuclear magnetic flowmeter 1 according to the invention is schematically illustrated in FIG. 2. As opposed to the embodiment illustrated in FIG. 1, the pre-magnetization device 3 has a several rotating magnetic arrangements 5. Six such magnetic arrangements 5 are illustrated, however, the invention is not limited to a certain number of magnetic arrangements 5. Each of the magnetic arrangements 5 generates a magnetic field in a certain strength and direction. The magnetic fields of adjacent rotating magnetic arrangements 5 can be parallel or anti-parallel to one another and it is also possible that a magnetic unit 5 does not generate a magnetic field. The effective pre-magnetization section is defined by the choice of orientation of adjacent magnetic arrangements 5. Both a first pre-magnetization section 6 and a second pre-magnetization section 7 are illustrated. As opposed to the pre-magnetization section 6, 7 according to the first embodiment, both pre-magnetization sections 6, 7 have a different starting point and a common ending point. Hence, the first measuring plane 8 and the second measuring plane 9 coincide in one spatial plane in the measuring device 4. 2D tomography is used in the measuring planes 8 and 9. It is also possible to implement tomography with layering the z direction.

Figure 3:
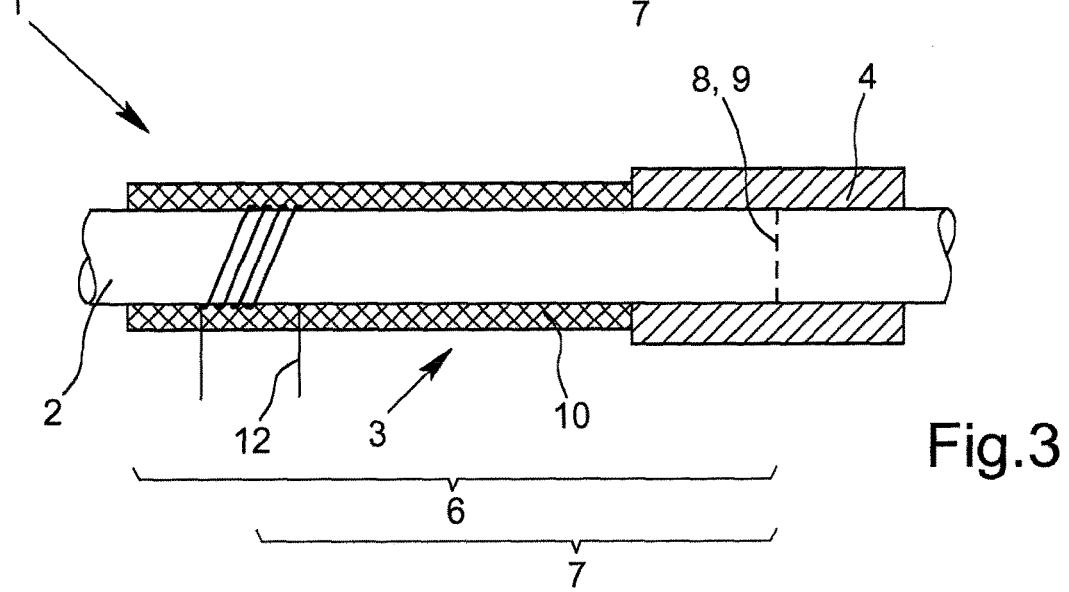
FIG. 3 is a schematic illustration of a third preferred embodiment of the nuclear magnetic flowmeter according to the invention.

A third embodiment of the flowmeter 1 according to the invention is illustrated in FIG. 3. The medium, of which the flow is to be measured, flows through the measuring tube 2. Analog to both embodiments described above, the flowmeter contains a pre-magnetization device 3 and a measuring device 4. In the embodiment illustrated in FIG. 3, the pre-magnetization device 3 contains one permanent magnet 10 or several permanent magnets 10 for generating a magnetic field interfusing the medium. Furthermore, the pre-magnetization device 3 contains a RF coil 12 generating a pulse destroying the magnetization of the medium or a pulse sequence destroying the magnetization of the medium. The magnetization generated in the area between the setting in of the pre-magnetization device 3 and the spoil coil 12 is destroyed again by the spoil pulse, so that the beginning of a "new" pre-magnetization section is located at the position of the spoil coil 12.

The two pre-magnetization sections 6, 7 of different lengths have—as shown—a different beginning, which allows them—as shown in FIG. 3—to have the same ending. The measuring plane 8 and the measuring plane 9 coincide in one single spatial plane in the measuring device 4. 2D tomography is implemented in the measuring planes 8 and 9. It is also possible to implement tomography with layering in the z direction.

Figure 4:
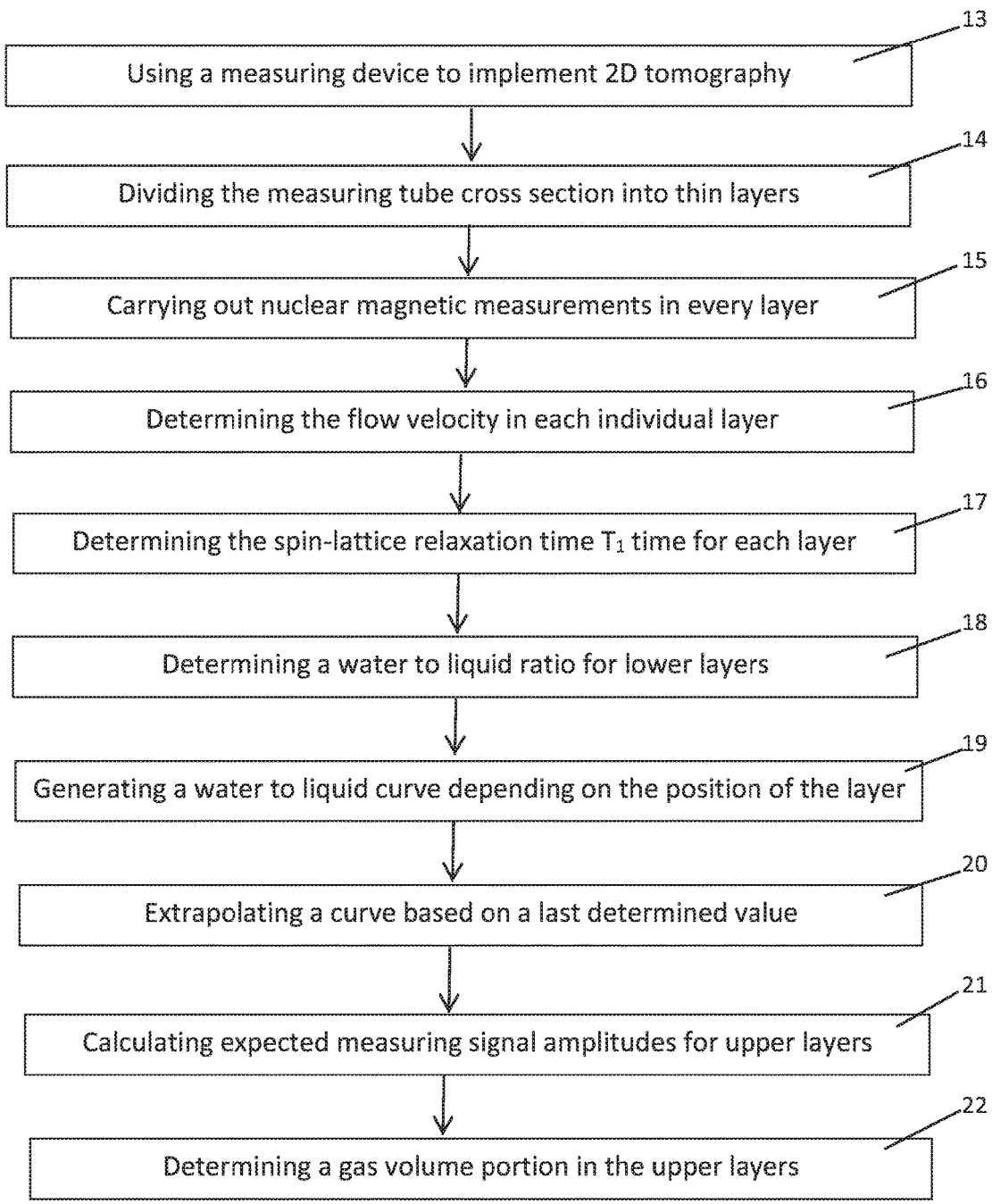
FIG. 4 is a flow chart of an embodiment of the method according to the invention.

FIG. 4 shows a flow chart of a method according to the invention for determining the flow of a multi-phase medium flowing through a measuring tube with a nuclear magnetic flowmeter having the pre-magnetization device 3 and the measuring device 4, the pre-magnetization device 3 having at least two pre-magnetization sections with different known lengths $L_1, L_2 \ldots L_n$, the method comprising:

using the measuring device to implement 2D tomography at the end of each pre-magnetization section in a measuring tube cross sectional plane in a z direction (step 13), dividing the measuring tube cross sectional plane into thin layers in relation to the measuring tube diameter (step 14), carrying out nuclear magnetic measurements in every layer for determining measuring signals with at least two pre-magnetization sections of different lengths (step 15), determining the flow velocity in each individual layer using the measuring signals (step 16), c time using the signal ratios of the amplitudes of the measuring signals in each layer (step 17), determining a water to liquid ratio for lower layers in the measuring tube 2 layer for layer from bottom to top in the measuring tube (step 18), generating a water to liquid curve depending on the position of the layer in the measuring tube 2 using the determined values determined in step 18 (step 19), then extrapolating a curve based on a last determined value over the entire measuring tube of cross section (step 20), calculating expected measuring signal amplitudes for the upper layers in the measuring tube of the curve extrapolated in step 20 (step 21), and determining a gas volume portion in the upper layers using a difference between the expected measuring signal amplitude and the actual measuring signal amplitude (step 22).

What is claimed is:

1. A method for determining the flow of a multi-phase medium flowing through a measuring tube with a nuclear magnetic flowmeter having a pre-magnetization device and a measuring device, the pre-magnetization device having at least two pre-magnetization sections with different known lengths $L_1, L_2, \ldots L_n$, the method comprising:

using a measuring device that implements 2D tomography at the end of each pre-magnetization section in measuring planes perpendicular to a longitudinal axis of the measuring tube, identically dividing the measuring planes into voxels, the dimensions of the voxels being chosen such that only one phase of the medium flows in each voxel, carrying out nuclear magnetic measurement for determining measuring signals, determining the flow velocity of the medium in each voxel in each measuring plane, determining an average flow velocity of the medium for each voxel over all measuring planes from determined values of the flow velocity of each corresponding voxel of the individual measuring planes, determining a signal ratio of measuring signals of each corresponding voxel of the different measuring planes relative to one another, and with the known values for the lengths $L_1, L_2 \ldots L_n$ of the pre-magnetization sections, determining spin-lattice relaxation time $T_1$ in each voxel using the signal ratios.

2. The method according to claim 1, wherein a respective hydrogen index HI in each voxel is determined with the respective spin-lattice relaxation time $T_1$ and wherein using the spin-lattice relaxation time $T_1$ and the hydrogen index HI, different phases of the medium and sections of the different phases are determined.

3. The method according to claim 2, wherein the flow rates are determined by integration over the different sections of the medium and multiplication with the respective flow velocities.

4. The method according to claim 1, wherein the nuclear magnetic measurement is implemented with a Carr Purcell Meiboom Gill (CPMG) sequence.

5. The method according to claim 1, wherein the velocity of the medium in every voxel in each plane is determined using the "convective decay" method.

6. The method according to claim 1, wherein amplitudes of the measuring signals at a time t =0 are used for determining the signal ratios.

7. The method according to claim 1, wherein a temporal course of the measuring signals is used for determining the signal ratio.

8. The method according to claim 1, wherein the at least two pre-magnetization sections are implemented by variable RF coils and wherein the measuring planes at the end of each pre-magnetization section are realized by different planes.

9. The method according to claim 1, wherein the at least two pre-magnetization sections are implemented by rotating magnetic arrangements and wherein the measuring planes at the end of each pre-magnetization section are realized in a single spatial plane.

10. The method according to claim 1, wherein the at least two pre-magnetization sections are implemented by RF coils transmitting spoil pulses and wherein the measuring planes at the end of each pre-magnetization section are realized in a single spatial plane.

11. A method for determining the flow of a multi-phase medium flowing through a measuring tube with a nuclear magnetic flowmeter having a pre-magnetization device and a measuring device, the pre-magnetization device having at least two pre-magnetization sections with different known lengths $L_1, L_2, \ldots L_n$, the method comprising:

using a measuring device that implements 2D tomography at the end of each pre-magnetization section in a measuring tube cross sectional plane in a z direction, dividing the measuring tube cross sectional plane into thin layers in relation to the measuring tube diameter, carrying out nuclear magnetic measurements in every layer for determining measuring signals with at least two pre-magnetization sections of different lengths, determining the flow velocity in each individual layer using the measuring signals, and determining the spin-lattice relaxation time $T_1$ time using the signal ratios of the amplitudes of the measuring signals in each layer.

12. The method according to claim 11, wherein the portions of the individual phases in the medium are determined using the absolute amplitudes of the measuring signals.

13. The method according to claim 11, wherein a water to liquid ratio for lower layers in the measuring tubes is determined layer for layer from bottom to top in the measuring tube, wherein a water to liquid curve depending on the position of the layer in the measuring tube is generated using the determined values, wherein a curve is extrapolated based on a last determined value over the entire measuring tube cross section, wherein expected measuring signal amplitudes for the upper layers in the measuring tube are calculated from the extrapolated curve, and wherein a gas volume portion in the upper layers is determined using a difference between the expected measuring signal amplitude and the actual measuring signal amplitude.

14. Nuclear magnetic flowmeter for determining the flow of a medium flowing through a measuring tube, comprising:
a pre-magnetization device and
a measuring device, wherein the pre-magnetization device implements at least two pre-magnetization sections of differing lengths with the lengths $L_1, L_2, \ldots L_n$, and wherein the measuring device is adapted to implement 2D tomography at the end of each pre-magnetization section either in a measuring plane perpendicular to a longitudinal axis of the measuring tube or in a measuring tube cross sectional plane in a z-direction.

15. Nuclear magnetic flowmeter according to claim 14, further comprising variable RF coils by which the different lengths $L_1, L_2, \ldots L_n$ of the pre-magnetization section are implemented and wherein the measuring planes at the end of every pre-magnetization section fall in the area of the respective RF coil.

16. Nuclear magnetic flowmeter according to claim 14, further comprising rotating magnetic arrangements by which the different lengths $L_1, L_2, \ldots L_n$ of the pre-magnetization section are implemented and wherein the measuring planes at the end of each pre magnetization section are realized in a single spatial plane.

17. Nuclear magnetic flowmeter according to claim 14, further comprising variable RF coils which transmit spoil pulses by which the different lengths $L_1, L_2, \ldots L_n$ of the pre magnetization section are implemented, and wherein the measuring planes at the end of each pre-magnetization section are realized in a single spatial plane.

* * * * *